United States Patent [19]
Mohajer

[11] Patent Number: 5,022,408
[45] Date of Patent: Jun. 11, 1991

[54] COMBINATION EXO/ENDOCERVICAL SAMPLER

[76] Inventor: Reza S. Mohajer, 3115 W. Shore Dr., Orchard Lake, Mich. 48033

[21] Appl. No.: 512,840

[22] Filed: Apr. 23, 1990

[51] Int. Cl.⁵ .......................................... A61B 10/00
[52] U.S. Cl. ..................................... 128/756; 128/759
[58] Field of Search ............... 128/756, 757, 759, 632, 128/749; 15/159 A; 606/161

[56] References Cited

U.S. PATENT DOCUMENTS

| | | | |
|---|---|---|---|
| 3,774,590 | 11/1973 | MacDonald | 128/757 |
| 3,961,620 | 6/1976 | Schack | 128/757 |
| 4,054,127 | 10/1977 | Milan | 128/757 |
| 4,127,113 | 11/1978 | Nollan | 128/756 |
| 4,700,713 | 10/1987 | Kist | 128/756 |
| 4,754,764 | 7/1988 | Bayne | 128/756 |
| 4,759,376 | 7/1988 | Stormby | 128/756 |
| 4,762,133 | 8/1988 | Bayne | 128/756 |
| 4,873,992 | 10/1989 | Bayne | 128/756 |
| 4,888,845 | 12/1989 | Ramm | 15/159 A |

FOREIGN PATENT DOCUMENTS

| | | | |
|---|---|---|---|
| 1429689 | 3/1976 | United Kingdom | 128/757 |
| 2208603 | 4/1989 | United Kingdom | 128/756 |

*Primary Examiner*—Kyle L. Howell
*Assistant Examiner*—Robert L. Nasser, Jr.
*Attorney, Agent, or Firm*—Krass & Young

[57] ABSTRACT

A method of and device for obtaining simultaneous samples of exo and endocervical cells. The device includes an elongated handle portion having a free end and a row of flags disposed proximate the end opposite the free end. The flags are rectangular in cross section and are disposed at an acute angle with respect to the handle portion. A substantially longer, relatively rigid filament is disposed on the handle portion proximate the row of flags at a point approximately diametrically opposite thereto. The filament serves as a stop when the device is inserted into the cervical os, and also scrapes the exocervical wall when the device is rotated 360°. Rotation of the device also causes the row of flags to engage the surface of the endocervix. When the device is removed, two separated cell samples are obtained.

13 Claims, 1 Drawing Sheet

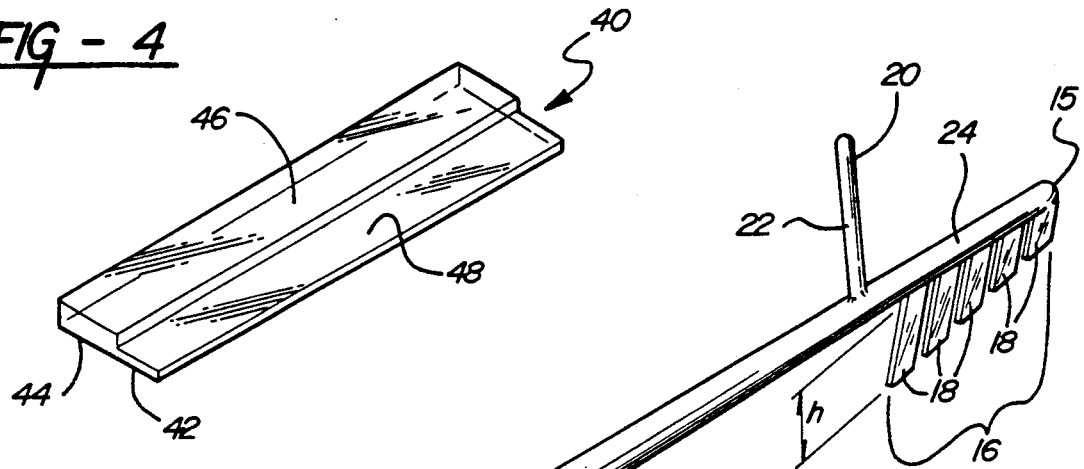
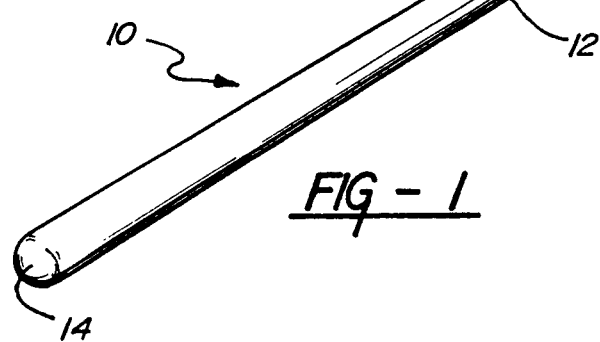
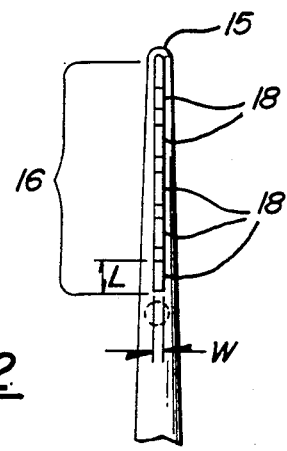
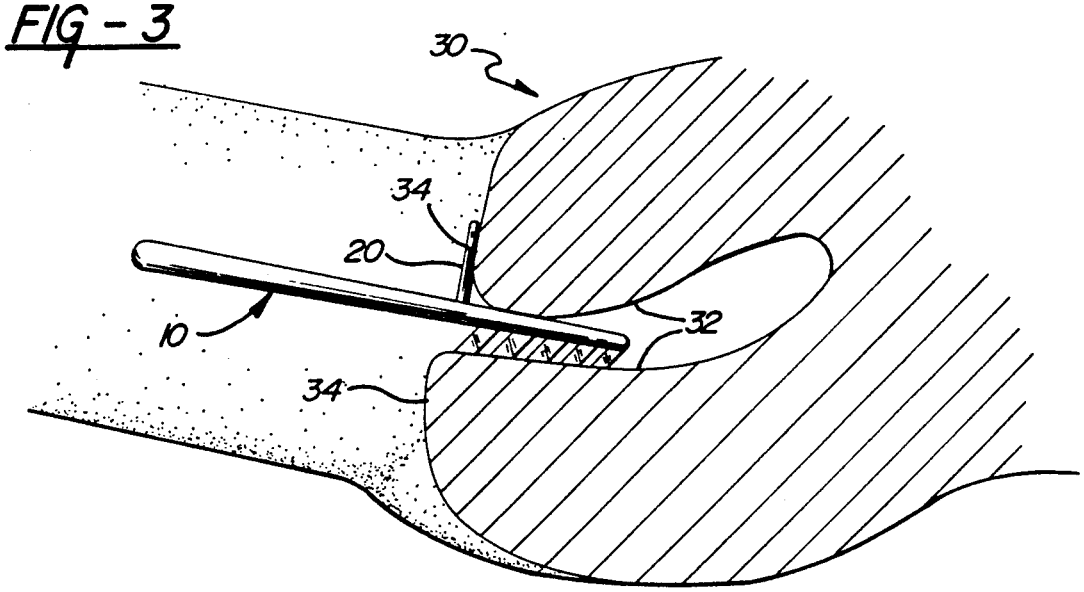

COMBINATION EXO/ENDOCERVICAL SAMPLER

BACKGROUND OF THE INVENTION

1. Field of the Invention

This invention relates to the field of collecting and preparing cervical smears for diagnostic purposes, and more particularly to a device and method for simultaneously collecting samples of both exocervical and endocervical cells.

2. Description of the Relevant Prior Art

Modern gynecological practice includes routine screening of women for the detection of inflammatory, pre-malignant and malignant changes in the cervix and uterus. Such screening provides the most effective means for early detection and even prevention of uterine cervical cancer. Because such routine screening has proven invaluable, many devices have been invented for obtaining diagnostic samples from the cervical area.

In their article entitled *Analysis of Five Sampling Methods for the Preparation of Cervical Smears*, Boon et al, *Acta Cytologica* (1988), pages 843–848, the authors describe five different devices for cervical cytologic sampling, and set forth the results of an analytic study undertaken to determine the efficacy of each device in obtaining acceptable samples. These five prior art devices include: (a) a modified Ayre spatula; (b) a cytological brush called the "Cytobrush" (see U.S. Pat. Nos. 3,881,464 and 4,759,376 for descriptions of such brushes), used in conjunction with the spatula; (c) a device called a "Cytopick," having a tip on one end and a spatula on the other; (d) a moistened cotton swab in combination with the spatula; and (e) a Cervex Brush, such as that described in U.S. Pat. No. 4,700,713.

The referenced article emphasizes that the sampling method utilized has a great impact on the quality of the cervical smear, "a decisive factor in the efficacy of population screening [for uterine cervical cancer.]" According to the article, the presence of endocervical cells is necessary for an adequate smear. The endocervical cells are, characteristically, glandular-type cells, in contrast to exocervical cells, which are squamous cells. As the authors emphasize, some of the sampling methods described are more effective in obtaining the important endocervical cells than are others. In particular, the spatula alone or in combination with the moistened cotton swab fails to produce adequate smear samples due to the absence of endocervical cells. In contrast, both the Cytobrush and the Cytopick exhibited superior performance in obtaining adequate smear samples containing endocervical cells.

It should be noted that most of the devices described in the referenced article were not capable of taking simultaneous samples from both the exocervix and the endocervix. The spatula, for example, is used by rotating it on the ectocervix. It does not penetrate the cervical os to any significant degree and, hence, does not sample the endocervix. The Cytobrush and Cytopick tip penetrate the cervical os to obtain endocervical samples. In order to obtain exocervical samples, either a separate device such as a spatula or a spatula disposed on the other end of the Cytopick must be used. Likewise, the relatively ineffective cotton swab is used to penetrate the endocervix, but does not provide an exocervical sample.

Of the methods described in the referenced article, only the Cervex Brush simultaneously samples both the exo and endocervix. This is possible because the individual bristles of the Cervex Brush are arranged roughly radially and parallel to the stem of the device. The bristles have at least one longitudinal sharp edge. By inserting the brush, the center bristles penetrate the cervical os and scrape the wall of the endocervix, while the outer brushes remain outside the cervical os and abut the exocervical wall, scraping the surface thereof to provide simultaneous exo and endocervical samples. However, as reported in the afore-referenced article, the Cervex brush achieved only moderate results in obtaining endocervical cell samples. This may be attributable to the fact that the bristles of the Cervex brush are relatively thick and tend to collect excess mucous which obscures all samples. Furthermore, this brush does not penetrate the full 2 cm depth of the average endocervix and because of its shape, does not contact and sample the wall of the encocervical canal.

Other prior art devices are known which are designed to effectively obtain endocervical cell samples. For example, the so-called "Bayne Brush" of U.S. Pat. No. 4,762,133 shows, in a preferred embodiment, two brushes attached to the end of the handle, the two brushes projecting at right angles from each other. One brush is inserted into the endocervix, while the perpendicular brush remains outside the cervical os. The device is rotated, thereby causing the bristles of the first brush to sweep the inside of the endocervix and collect cells therefrom, and the second brush to scrape the surface of the exocervical wall, thereby obtaining exocervical cells simultaneously. While the device is, admittedly, effective in obtaining adequate cervical smears, it has a number of drawbacks. First, the relatively rigid bristles of the two brushes often cause bleeding, which results in obscure slides and imperils the accuracy of the results. Furthermore, atypical and immature cell groups may be present in cytobrush smears since this brush tends to remove immature cells from deeper layers of cervical tissue. These cells are not readily recognized by cytotechnicians and can lead to confusing and inaccurate diagnostic reports and may necessitate further invasive procedures. In fact, the medical profession has come to recognize the "brush effect" wherein atypical cells are noted in collected samples but cannot be correlated with any lesions of the cervix. Additionally, the Bayne Brush is complex in construction and relatively expensive. Despite these disadvantages, the Bayne Brush has met with some acceptance in the gynecological field.

Another cervical brush is described in U.S. Pat. No. 4,127,113. This patent describes a device with a rigid stem having a handle at one end and an integral brush disposed on the other end. The brush has a flexible spine and fine, flexible bristles which extend in a row along the spine of the brush. There is a flat blade at the root of the spine which serves as a locator and stop at the entrance to the cervix. The device is inserted into the cervix up to the stop, and rotated so that the brush accumulates sample material from substantially the entire inner wall of the endocervix. The brush is subsequently wiped across a slide to deposit the sample for examination.

As described and disclosed in U.S. Pat. No. 4,127,113, the cervical brush does not provide any structure for simultaneously obtaining an exocervical sample. The flat blade merely serves as a stop; it is not wiped across the slide. Yet, an adequate cervical sample should contain "cells from the squamous epithelium of the vaginal portion of the cervix, from the squamocolumnar junction (also known as the transformation zone), and from the endocervical epithelium." *The Papanicolaou Test for Cervical Cancer Detection—a Triumph and a Tragedy,* Leopold G. Koss, M.D., JAMA (1989), page 737, 738. Hence, in order to obtain an adequate smear, it would be necessary to use the cervical brush of the referenced patent in conjunction with another device, such as a spatula, for obtaining exocervical cells. This dual procedure is, obviously, time consuming, inefficient and uncomfortable for the patient. Furthermore, significant drying of the first sample can occur during the time the second sample is being prepared resulting in an inaccurate or unreadable slide.

It would be desirable to provide a cervical sampling device which is capable of simultaneously and effectively obtaining samples of both endocervical and exocervical cells.

It would also be desirable to provide such a device which is inexpensive and unitary in construction, which does not cause bleeding in the patient, and which is comfortable for the patient during insertion and use.

SUMMARY OF THE INVENTION

The device and method of the present invention have been designed to overcome the disadvantages of the prior art noted. To that end, there is provided a combination exo and endocervical sampler. It comprises an elongated handle portion having a free end which is adapted to be grasped by the clinician. A row of flexible flags, preferably flat in cross section are disposed at the end of the handle portion opposite the free end and projecting therefrom. Preferably, the flags project toward the free end of the handle portion at an acute angle with the handle portion. The flags are thin and flexible enough so that they may be easily inserted into the endocervical canal through a stenotic cervical os. An exocervical filament is disposed at a location on the handle medial of said row of flags and proximate thereto. The filament is substantially longer than any of the flags and has sufficient stiffness to act as a stop when the sampler is inserted into the vaginal canal of the patient. The purpose of the long filament is to sweep the exocervical wall as the device is rotated after it has been properly inserted.

Preferably, the filament is disposed on the handle portion at a point thereon substantially diametrically opposite the row of flags. Hence, it will project generally away from the row of flags. It is thought that this arrangement will help in insuring proper contact between the surfaces of the flags and the surface of the endocervix after the device has been inserted.

BRIEF DESCRIPTION OF THE DRAWINGS

The following detailed description may best be understood by reference to the following drawing in which:

FIG. 1 is a perspective view of the cervical sampling device of the present invention;

FIG. 2 is a detail, end-on view of the row of flags of the device of FIG. 1 particularly illustrating their cross-sectional configuration;

FIG. 3 shows the device of the present method in use; and

FIG. 4 is a specially designed microscopic slide suitable for use with the device of the present invention.

DETAILED DESCRIPTION OF THE PREFERRED EMBODIMENT

Throughout the detailed description, identical reference numbers are used to refer to the same element of the present invention shown in multiple figures thereof. Referring now to the drawing, and in particular to FIGS. 1 and 2, there is shown a cervical sampler 10 constructed according to the instant invention. The cervical sampler 10 comprises an elongated handle portion 12 having a free end 14. A row 16 of flexible, endocervical flags 18 are disposed on the end 15 of handle portion 12 opposite free end 14. As is shown in FIG. 2, each of the flags 18 is configured to have a rectangular cross section, with the width W of each flag being substantially less than the height H thereof. The configuration of the flags 18 is optimized in this manner to minimize the problems noted with the bristles of prior art devices. Due to their thinness, the flags are relatively flexible and will not penetrate deeper layers of cervical tissue or cause bleeding or distortion of the cell samples when the cervical sampling is done. Furthermore, their relatively great height provides a broad surface for obtaining an adequate sample. Moreover, since the flags 18 are disposed along handle portion 12 in a row 16, they only project from one side of handle portion 12. This reduces the diameter of the device and permits easier insertion thereof.

It is desirable that the flags 18 project from handle portion 12 at an acute angle therewith, as is shown in FIG. 1. In general, the flags 18 will project from the handle 12 at an angle of approximately 45° to 90°, although still smaller angles may be employed. Preferably, the flags 18 will depend from handle portion 12 and project toward free end 14 at an angle of approximately 75° to the handle (i.e. 15° off normal). Furthermore, the flags 18 of row 16 are tapered in length such that the flag 18 having the shortest length is closest to opposite end 15 and the flag 18 having the greatest length L is closest free end 14. By arranging and configuring the flags 18 in this tapering, angled manner, the device 12 is able to readily penetrate a stenotic cervical os and obtain a more complete sampling from various portions of the endocervix. Since the flags 18 are flexible, their angled relation to the handle portion 12 presents no particular obstacle to removal of the device 10.

Disposed on handle portion 12 proximate row 16 of flags 18 and medial thereof is an exocervical filament 20. Exocervical filament 20 has a length substantially longer than that of any of the flags 18. Furthermore, in contrast to flexible flags 18, it is relatively stiff. To that end, it is formed with a thickened spine 22 for increased rigidity. Due to its rigidity, filament 20 serves as a stop when the opposite end 15 of device 10 is inserted into the cervical os of a patient. In the preferred embodiment shown in FIG. 1, the filament 20 is disposed on handle portion 12 at a point approximately diametrically opposite the row 16 of flags 18. Filament 20 is arranged in this manner with respect to row 16 to assist in engagement of the flags 16 with the endocervical surface 32 when the device is in use, as is shown in FIG. 3.

Preferably, cervical sampler 10 is unitary in construction in contrast to the prior art brush devices described in the Background section. This unitary construction results in ease of manufacture and lower cost, a critical factor for a device commonly used in mass screening. Device 10 may be molded of any of a number of synthetic polymeric resins such as polyethylene, polypropylene, polyester, nylon, polystyrene, polyvinylacetate, or a block copolymer of a polybutylene terepthalate polyester and a long chain polyether glycol. One such commercially available material is a block copolymer consisting of a higher (crystalline) segment of polybutylene terepthalate and a soft (amorphous) segment based on long chain polyether glycols. Such materials are sold by the DuPont Corporation under the trade name Hytrel. Hytrel polymers are available in FDA approved food grades.

As is obvious from FIG. 1, the preferred embodiment of the present invention tapers in diameter from the free end 14 to the opposite end 15. Preferably, there is a narrowed portion 24 of handle portion 12 upon which row 16 of flags 18 is disposed. The device is larger in diameter at free end 14 and configured so it may easily be grasped by the user. Narrowed portion 24 significantly reduces the total diameter of the device 10 so that it may be more easily inserted, used, and removed. The overall length of the device 10 is approximately 16-17 centimeters. The filament 20 has an approximate length of 2 centimeters. The diameter of the device 10 at the narrowed portion varies from between approximately 1 to approximately 4 millimeters.

The manner of use of the device is illustrated in FIG. 3. The vaginal canal is dilated in the usual manner by means of a speculum (not shown). The device 10 is then inserted into the cervix 30 until the filament 20 abuts the exocervical wall 34. At this point, the head of the device will be inside the endocervix 32 and the row of flags 18 will engage the endocervix 32. The device 10 is then rotated through approximately 360° so that the flags 18 will sweep the surface of the endocervix, while the filament 20 sweeps the exocervical wall 34. Thus, simultaneous and separated samples of both endo and exocervical cells are obtained. The device is then simply withdrawn from the cervix 30. Separation of the samples is important since the endocervix can give rise to adenocarcinoma while the exocervix can manifest squamo-cell carcinoma, and the cell types of the two are distinct and more easily diagnosed if separated.

Preferably, the device 10 containing the separated exo and endocervical samples is immediately wiped across a specially designed slide 40, illustrated in FIG. 4. Slide 40 is divided either longitudinally, as shown, or latitudinally into two sections, a lower portion 42 and a higher portion 44 which are disposed in step-wise fashion. By wiping the loaded sampler 10 across the length of the slide 40, an exocervical sample will be deposited on the surface 46 of higher portion 44, while an endocervical sample will be simultaneously deposited on the surface 48 of lower portion 42. A fixative is immediately applied to the slide 40 in the usual manner. The separated surfaces 46, 48 of slide 40 may then be examined separately for abnormalities. By maintaining separation of the endo and exocervical samples throughout the sampling procedure and preparation of the slide, more accurate results will be obtained during examination of the separated cell samples since different cell types and hence different cancers occur in the exo and endocervix.

While the present invention has been described with reference to certain embodiments and exemplifications therein, the scope of the invention is not limited to those embodiments and exemplifications. For example, the number of flags may differ from those shown here. Likewise, the cross-sectional shape of the flags need not be strictly rectangular; in some instances, it may be advantageous to configure the flags to have a rhomboidal or trapezoidal cross section, or to have rounded corners. In other instances, the flags may be dimensioned so that their length is less than, or equal to their height. Also, the exocervical sampling filament may be disposed other than in a 180° opposed relationship with the flags. Doubtless, other variations may occur to one skilled in the art without departing from the teachings of the present invention. The true scope of the invention is defined solely by the claims appended hereto.

I claim:

1. A combination exo-endocervical sampler comprising:
   an elongated handle portion having a free end;
   a plurality of flexible flags each of said flags having a length "L", a height "H" and a width "W" such that W is less than L or H, said flags disposed in a mutually coplanar row at an end of the handle portion opposite said free end and projecting therefrom at an acute angle for insertion into the endocervical canal; and
   an exocervical filament disposed at a location on said handle portion medial of said row and proximate thereto, said filament having a length substantially greater than the length of any of said flags and having sufficient stiffness to act as a stop when the sampler is inserted.

2. The device of claim 1 wherein the row of flags depends from the handle portion at an acute angle therefrom.

3. The device of claim 1 wherein the sampler is unitary in construction.

4. The device of claim 3 wherein each of the flags has a flat cross section.

5. The device of claim 1 wherein the row of flags taper in length to a maximum toward said free end of the handle.

6. The device of claim 5 wherein the longest flag has a length of approximately 0.4 centimeters and the shortest a length of approximately 0.1 centimeters.

7. The device of claim 6 wherein the filament has a length of approximate 2 centimeters.

8. The device of claim 7 wherein the filament further comprises a thickened spine for increased rigidity.

9. The device of claim 1 wherein the filament is disposed on the handle portion on a point thereon substantially diametrically opposite the row of flags.

10. The device of claim 1 wherein the sampler is formed of a synthetic polymeric resin selected from the group consisting essentially of: polypropylene, polyethylene, polyester, nylon, polystyrene, polyvinylacetate, and polybutylene terepthalate/polyether glycol block copolymer, and combinations thereof.

11. The device of claim 1 wherein the handle further comprises a narrowed portion proximate the end opposite the free end, said row of flags being disposed on said narrowed portion.

12. A cervical sampler comprising:
   an elongated handle portion defining a longitudinal axis;
   a plurality of flexible flag members, each flag member being of rectangular cross section and having a length "L", a height "H" and a width "W" such that W is less than H or L, said flags disposed in a mutually coplanar row proximate one end of said handle portion so that the lengths thereof are aligned with said longitudinal axis, said flags projecting therefrom at an acute angle.

13. A cervical sampler as in claim 12 further including an exocervical sampling filament disposed on said handle portion perpendicular to said longitudinal axis, said filament medial of, and proximate to said row of flags.

* * * * *